United States Patent [19]
Shell et al.

[11] Patent Number: 5,972,389
[45] Date of Patent: Oct. 26, 1999

[54] GASTRIC-RETENTIVE, ORAL DRUG DOSAGE FORMS FOR THE CONTROLLED-RELEASE OF SPARINGLY SOLUBLE DRUGS AND INSOLUBLE MATTER

[75] Inventors: John W. Shell, Hillsborough; Jenny Louie-Helm, Union City, both of Calif.

[73] Assignee: DepoMed, Inc., Foster City, Calif.

[21] Appl. No.: 08/716,906

[22] Filed: Sep. 19, 1996

[51] Int. Cl.[6] .............................. A61K 9/16; A61K 47/34
[52] U.S. Cl. .......................................... 424/501; 424/426
[58] Field of Search ..................................... 424/486, 426, 424/428, 429, 499–501; 514/951–52; 428/402

[56] References Cited

U.S. PATENT DOCUMENTS

| | | | |
|---|---|---|---|
| 4,404,183 | 9/1983 | Kawata et al. | 424/501 |
| 5,007,790 | 4/1991 | Shell | 424/451 |
| 5,273,758 | 12/1993 | Royce | 424/465 |
| 5,545,423 | 8/1996 | Soon-Shiong et al. | 424/484 |

FOREIGN PATENT DOCUMENTS

| | | |
|---|---|---|
| 0 322 392 | 6/1989 | European Pat. Off. . |
| WO 93/18755 | 9/1993 | WIPO . |
| WO 95/31186 | 11/1995 | WIPO . |
| 96/32097 | 10/1996 | WIPO . |

OTHER PUBLICATIONS

Davis, et al., "Transit of pharmaceutical dosage forms through the small intestine", *Gut*, 27 (8):886–892 (1986).

Fara, "Physiological limitations: gastric emptying and transit of dosage forms" in: *Rate Control in Drug Therapy*, L.F. Prescott, et al., Eds., Churchill Livingstone, New York (1985).

Hunt, et al., "A Relation Between the Chain Length of Fatty Acids and the Slowing of Gastric Emptying", *J. Physiol.*, 194:327–336 (1968).

Meyer, "Gastrointestinal Structure and Function on Postcibal Transit of Food and Drug Particles" in: *Drug Delivery to the Gastrointestinal Tract*, J.G. Hardy, et al., Eds., Ellis Harwood, Ltd., Chichester, Chapter 3 (1989).

Sleisinger, *Gastrointestinal Disease*, 4th ed., W.B. Saunders, pp. 679–681 (1989).

*Primary Examiner*—Edward J. Webman
*Attorney, Agent, or Firm*—Townsend and Townsend and Crew LLP

[57] ABSTRACT

Controlled-release oral drug dosage forms that comprise a tablet or capsule containing a plurality of particles of a solid-state drug dispersed in a swellable/erodible polymer, such as poly(ethylene oxide) are described. Once ingested, the tablet or capsule disintegrates to disperse the particles within the stomach where they imbibe water to cause them to swell and promote retention in fed-mode-induced patients. As the gastric-retained dosage form gradually erodes, the drug is released in a controlled manner to the stomach for treatment of local disorders, and to the upper gastrointestinal tract where it becomes available for absorption in a controlled and therapeutic manner. Drug-containing vesicles, such as liposomes or nanoparticles or enteric-coated drug particles, can also be delivered to the gastrointestinal tract in a controlled manner using the gastric-retentive dosage forms of the present invention.

33 Claims, 3 Drawing Sheets

GASTRIC-RETENTIVE, ORAL DRUG DOSAGE FORMS FOR THE CONTROLLED-RELEASE OF SPARINGLY SOLUBLE DRUGS AND INSOLUBLE MATTER

FIELD OF THE INVENTION

The present invention relates generally to the field of pharmacology and, in particular, to drug dosage forms that are retained in the stomach and gradually deliver sparingly soluble drugs or insoluble, particulate matter over a time period of several hours. More particularly, the present invention provides swellable polymer systems designed to deliver sparingly soluble drugs, insoluble or particulate matter and soluble drugs rendered less soluble by hydrophobicity enhancing agents into the gastrointestinal (G.I.) tract. The drug or particulate matter is released into the stomach as the polymer gradually erodes and, thus, the rate at which the drug or insoluble, particulate matter is delivered is determined by the rate of polymer erosion.

BACKGROUND OF THE INVENTION

This invention is an improvement over the sustained-release oral drug dosage forms described in U.S. Pat. Nos. 5,007,790 and copending U.S. Ser. No. 08/453,144 which was filed May 30, 1995. The dosage forms described therein consist of a plurality of solid particles composed of a solid drug dispersed in either a crosslinked or non-crosslinked, hydrophilic, water-swellable polymer. In these dosage forms, the polymers in which the drug is dispersed imbibe water, causing the particles to swell which promotes their retention and also allows the drug contained in the particles to dissolve and diffuse from the particles. Over a period of many hours, the drug diffuses from the particles at a rate related to the dissolution rate of the drug. However, only after the drug has substantially dissipated from the dosage form, does the polymer dissolve.

Poly(ethylene oxide) and hydroxypropyl methylcellulose polymers have been used in the pharmaceutical industry for controlled drug delivery systems including, for example, oral drug delivery systems. However, such polymers have not previously been used in gastric retentive, oral drug delivery systems.

SUMMARY OF THE INVENTION

In contrast to the systems of the prior art, the present invention provides erodible, gastric-retentive drug dosage forms for the delivery of: sparingly soluble drugs; insoluble, particulate matter from which incorporated drugs are later released; or soluble drugs that are rendered sparingly soluble when combined with a drug delivery modifier. More particularly, the present invention provides swellable polymer systems designed to deliver sparingly soluble drugs, insoluble or particulate matter and soluble drugs rendered less soluble by hydrophobicity enhancing agents into the gastrointestinal (G.I.) tract as a result of the gradual erosion of the polymer. Moreover, the swelling properties of the polymers are important in that they allow the dosage forms to be retained in the stomach where they effectively deliver drugs on a continuous basis to the stomach, duodenum and upper sections of the small intestine where absorption is efficient.

As such, in one embodiment, the present invention provides a controlled-release or, alternatively, sustained-release oral drug dosage form for releasing a sparingly soluble drug into the stomach, the drug dosage form comprising a plurality of solid particles or pellets of a solid-state drug dispersed within a polymer that (i) swells unrestrained dimensionally via imbibition of gastric fluid to increase the size of the particles to promote gastric retention within the stomach of a patient in which the fed mode has been induced, (ii) gradually erodes over a time period of hours, with the erosion commencing upon contact with the gastric fluid, and (iii) releases the drug to the stomach and duodenum at a rate dependent on the erosion rate. When presented in the form of a tablet or capsule that maintains the solid particles in a packed mass prior to their ingestion, the tablet or capsule rapidly dissolves or disintegrates upon contact with the gastric fluid to permit the particles to disperse in the stomach.

In another embodiment, the present invention provides a controlled-release oral drug dosage form for releasing a vesicle-containing vesicle, i.e., insoluble, particulate matter, into the stomach, the dosage form comprising a plurality of solid particles of the vesicle-containing drug dispersed within a polymer that (i) swells unrestrained dimensionally via imbibition of water from gastric fluid to increase the size of the particles to promote gastric retention in the stomach of a patient in which the fed mode has been induced, (ii) gradually erodes over a time period of hours, the erosion commencing upon contact with the gastric fluid, and (iii) releases the insoluble particulate matter to the stomach and duodenum at a rate dependent on the erosion rate. Insoluble, particulate matter suitable for use in this embodiment include, but is not limited to, liposomes, nanoparticles, nanospheres and nanocapsules. For example, liposomes encapsulating an acid-labile or enzyme-labile soluble drug, such as a proteinaceous hormone (e.g., calcitonin), an antigen, a peptide, or other drugs that otherwise would require administration by injection, such as erythropoietin, can be dispersed within a polymer to form an erodible, gastric-retentive drug dosage form of the present invention. In this regard, the erodible, gastric-retentive drug dosage form has the added beneficial properties associated with the use of vesicles. Such beneficial properties include protecting drugs against the degradative environment of the G.I. tract, overcoming a too rapid drug release rate due to high drug solubility, or targeting drugs to specific areas within the G.I. tract, such as Peyer's patches.

Particulate, insoluble matter suitable for use in this embodiment also includes solid particles that are granulations of a selected drug with an agent that serves to delay dissolution of the granules until they have passed out of the acidic environment of the stomach. Such "enteric coated" agents include, but are not limited to, methacrylic acid copolymer, types A, B, or C, which are commercially available from Rohm Tech, Inc. (Malden, Mass.), and water-based dispersions of cellulose acetate phthalate latex, which is commercially available from Eastman Fine Chemicals (Kingsport, Tenn.). As such, in yet another embodiment, the present invention provides a controlled-release oral drug dosage form for releasing an enteric-coated drug into the stomach of a patient, the dosage form comprising a plurality of solid particles of the enteric-coated drug dispersed within a polymer that (i) swells unrestrained dimensionally via imbibition of water from gastric fluid to increase the size of the particles to promote gastric retention in the stomach of a patient in which the fed mode has been induced, (ii) gradually erodes over a time period of hours, the erosion commencing upon contact with the gastric fluid, and (iii) releases the enteric-coated drug to the stomach and duodenum as a result of the erosion at a rate corresponding to the time period.

Other features, objects and advantages of the invention and its preferred embodiments will become apparent from the detailed description which follows.

DETAILED DESCRIPTION OF THE INVENTION AND PREFERRED EMBODIMENTS

Figure 1:
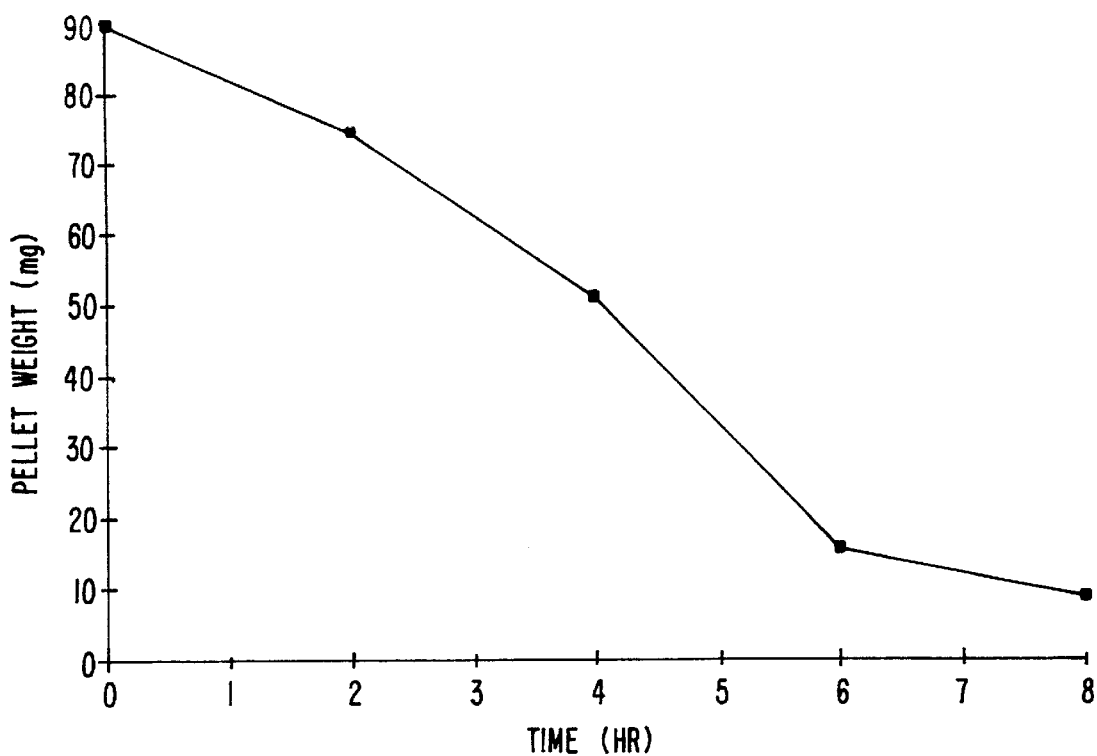
FIG. 1 illustrates the erosion of a 4-mm pellet containing 80% barium sulfate in Benecel® MP843 (hydroxypropyl methylcellulose).

The transit time through the gastrointestinal tract often limits the amount of drug available for absorption at its most efficient absorption site, or for local activity at one segment of the G.I. tract. The latter is particularly true when the absorption site is high in the G.I. tract, for example, when the required treatment is local in the stomach as is often the case with ulcers. As the solubility of the drug decreases, the time required for drug dissolution becomes less adequate and, thus, the transit time becomes a significant factor that interferes with effective drug delivery. To counter this, oral administration of sparingly soluble drugs is done frequently, often several times per day. Moreover, due to their insolubility, sparingly soluble or almost insoluble drugs cannot readily be delivered by either solution-diffusion or membrane-controlled delivery systems.

To overcome these problems, the erodible, gastric-retentive dosage forms of the present invention have been developed. The dosage forms of the present invention are effective for the continuous, controlled administration of drugs which have a low or sparing solubility in gastric fluid, and which are capable of acting either locally within the gastrointestinal tract, or systemically by absorption into circulation via the gastrointestinal mucosa. In addition, the dosage forms of the present invention are useful for delivering drugs incorporated into vesicles, such as liposomes, nanoparticles, proteinoid microspheres, pharmacosomes, etc. The dosage forms of the present invention are also useful for delivering drugs that have been granulated or coated with enteric coating material, so that they pass from the acid environment of the stomach before they can dissolve and become available for absorption. In this manner, the drugs are protected from acid and enzymes during the stomach transit time, so that they arrive intact in the upper part of the small intestine, yet in a controlled manner, due to the dosage form. As such, the dosage forms of the present invention generally consist of a drug or, alternatively, either a drug incorporated into a protective vesicle, or protected by an enteric coating, in combination with an erodible polymer that swells upon contact with the gastric fluid of the stomach.

Quite importantly, the dosage forms of the present invention result in a rate of drug release that is independent of the amount of water or gastric fluid present, above a minimum volume of a few cc's. This property of the dosage forms of the present invention is very useful with drugs that are sparingly soluble because the amount of drug which dissolves (and therefore becomes available for absorption) relates to the volume of fluid present. Unfortunately, this fluid volume varies greatly from patient to patient and, in addition, at different times of the day for any one patient. Thus, the disclosed dosage forms of the present invention allow for more uniform and predictable absorption of the incorporated drug. This characteristic is particularly important for poorly-soluble drugs such as phenytoin and carbamazepine which are anticonvulsant drugs used in epilepsy and for which, due to wide variation in drug absorption from patient-to patient, doctors must now titrate their patients individually to find the proper (i.e., safe and effective) regimen. In this regard, the dosage forms of the invention are useful for more-consistent delivery of sparingly soluble drugs that have a narrow therapeutic index, i.e., the toxic dose is not much more than the effective dose.

The rate at which the drug or, alternatively, the drug either in a protective vesicle or enteric coating is released to the gastrointestinal tract is largely dependent on the rate at which the polymer erodes. The polymer used in the dosage forms of the present invention should not erode and release the drug at too rapid a rate so as to provide a drug overdose or to cause the drug to pass through the gastrointestinal tract too fast (i.e., less than about four hours), nor should the polymer erode so slowly that too little of the drug is released to achieve the desired therapy. Thus, polymers having an erodibility that permits a rate of release that achieves the requisite pharmacokinetics for a desired duration are selected for use in the dosage forms of the present invention.

Polymers suitable for use in the present invention have the property of swelling as a result of imbibing water from the gastric fluid, and gradually eroding over a time period of hours. Since erosion of the polymer results from the interaction of fluid with the surface of the dosage form, erosion initiates simultaneously with the swelling process. The phrase "erosion commencing upon contact with the gastric fluid," as used herein, refers to that erosion resulting from the contact of the gastric fluid on the surface of the dosage form exposed to that fluid. While swelling and erosion occur at the same time, the rate for achieving maximum swelling should be faster than the rate the dosage form fully erodes. More particularly, swelling should be at a rate fast enough to allow the particles to be retained in the stomach, while erosion should be of a rate that provides the desired dosing of the drug being delivered.

The term "drug" is used herein to refer to any chemical that elicits a biochemical response when administered to a human or an animal. The drug may act as a substrate or product of a biochemical reaction, or the drug may interact with a cell receptor and elicit a physiological response, or the drug may bind with and block a receptor from eliciting a physiological response. The term "antigen," as used herein, refers to a drug that elicits an immune response. Moreover, the term "sparingly soluble," as used herein, refers to a drug having a solubility (measured in water at 37° C.) in the range of 0.001% to about 2% by weight, more preferably 0.001% to 0.5% by weight. The term "soluble", as used herein, refers to a drug having a solubility (measured in water at 37° C.) in the range of 2% to about 10% by weight, more preferably 2% to 5% by weight. The term "vesicle," as used herein, refers to a small (usually 0.01 to 1.0 mm), usually spherical, membrane-bound structure which may contain or be composed of either lipoidal or aqueous material, or both. Suitable vesicles include, but are not limited to, liposomes, nanoparticles, nanospheres, nanocapsules and microspheres composed of amino acids.

The term "fed mode," as used herein, refers to a state which is typically induced in a patient by the presence of food in the stomach, the food giving rise to two signals, one that is said to stem from stomach distension and the other a chemical signal based on food in the stomach. It has been determined that once the fed mode has been induced, larger particles are retained in the stomach for a longer period of time than smaller particles. Thus, the fed mode is typically induced in a patient by the presence of food in the stomach.

The dosage forms of the present invention are particularly useful for delivering drugs directly into the stomach for an extended period of time, for example, when the drug is preferentially absorbed there (e.g., ciprofloxacin), or for providing continuous, local-only (non-systemic) action, for example, when the drug is calcium carbonate, and which when incorporated into the dosage forms of the present invention becomes a non-systemic, controlled-release antacid. The dosage forms are also useful for delivering drugs continuously to the stomach that are only soluble in that portion of the gastrointestinal tract. For instance, the dosage forms of the present invention are useful for the delivery of calcium carbonate when it is intended to be used as a dietary supplement to prevent osteoporosis. This drug is soluble only in the stomach as a result of the presence of acid in only that portion of the gastrointestinal tract. With conventional dosage forms, the dwell time of the delivered agent in the stomach is limited usually to only about 20 to 40 minutes which, in turn, results in a calcium availability of only about 15 to 30%. As a consequence, extremely large dosage forms (2.5 grams), which are difficult for patients to swallow, are commonly utilized. In contrast, by providing controlled delivery for about 6 to 8 hours, plus gastric retention of from about 6 to 8 hours, the dosage forms of the present invention assure more complete bioavailability of elemental calcium from the administered drug, i.e., calcium carbonate. This results in a greater likelihood of patients receiving the intended dose and, also, avoids the need for impractically large dosage forms.

The dosage forms of the present invention are also useful for delivering drugs to treat local disorders of the stomach, such as those that are effective for eradicating *Helicobacter pylori* from the submucosal tissue of the stomach, to treat stomach and duodenal ulcers, to treat gastritis and esophagitis and to reduce risk of gastric carcinoma. The dosage forms of the present invention are particularly useful for the foregoing indications because they provide enhanced gastric retention and prolonged release. Drugs which can be delivered using the dosage forms of the present invention for the eradication of *H. pylori* include, but are not limited to, bismuth salts, such as bismuth subsalicylate and bismuth citrate; antibiotics, such as amoxicillin, tetracycline, chlarithromycin and thiamphenicol; metronidazole; and gastric acid lowering agents, such as omeprazole, ranitidine, cimetidine, and famotidine, as well as combinations of such drugs. In a preferred embodiment, a triple combination of bismuth subsalicylate, thiamphenicol and omeprazole are delivered using the dosage forms of the present invention for the eradication of *H. pylori*.

Drugs delivered from the gastric-retentive, controlled delivery dosage forms of the invention continuously bathe the stomach, duodenum and upper part of the small intestine for many hours. These sites, particularly the upper small intestine, are the sites of most efficient absorption for many drugs. As a consequence, the dosage forms of the present invention allow for sufficiently increased absorption so that drugs otherwise requiring injection can be made effective for oral administration. Such drugs include, but are not limited to, vancomycin, gentamycin and cefoxitin. In addition, by continually supplying the drug to its most efficient site of absorption, the dosage forms of the present invention allow for more effective oral use of peptide and protein drugs, such as calcitonin, erythropoietin, vasopressin, insulin, low molecular weight heparin, protease inhibitors and luteinizing hormone releasing hormone (LHRH) analogs.

Since the dosage forms of the present invention provide the drug by means of a continuous delivery instead of the pulse-entry delivery associated with conventional dosage forms, two particularly significant benefits result from their use: (1) a reduction in side effects from the drug(s); and (2) an ability to effect treatment with less frequent administration of the drug(s) being used. For instance, when administered in a conventional dosage form, the sparingly soluble drug nifedipine, a calcium channel blocker administered to treat arterial hypertension, is currently given three times daily to avoid side effects such as reflex tachycardia. However, using the dosage forms of the present invention, the number of daily doses can be decreased to one. Examples of other sparingly soluble drugs that can be advantageously delivered using the dosage forms disclosed herein include, but are not limited to, the following: acyclovir; alprazolam; phenytoin; carbamazepine; ranitidine; cimetidine; famotidine; cozapine; nizatidine; omeprazole; gemfibrozil; lovastatin; nitrofurantoin; cyclosporin; and fluoxitine.

As previously mentioned, the dosage forms of the present invention are particularly useful for delivering sparingly soluble drugs. However, in another embodiment, the dosage forms of the present invention can be used to deliver a drug incorporated into a protective vesicle. In this embodiment, the drug can be a sparingly soluble drug or, alternatively, a soluble drug which is rendered sparingly soluble or insoluble when incorporated into the protective vesicles. Suitable vesicles include, but are not limited to, liposomes, nanoparticles, nanospheres, nanocapsules and microspheres composed of amino acids.

By incorporating a drug either in a protective vesicle or enteric coating into the dosage form of the present invention, the benefits of gastric retention and gradual release to the G.I. tract are combined with the advantageous properties of the vesicle or enteric coating. Advantageous properties associated with the use of such agents include, for example, protecting the drug from the detrimental environment of the G.I. tract (e.g., degradative enzymes and low pH), enhancing drug absorption and/or altering drug solubility. In this context, the drug in combination with either agent is continuously and gradually released from the gastric-retentive system to bathe the duodenum and small intestine in a prolonged manner which is determined by the rate at which the polymer erodes. Moreover, in this context, less of the drug is required to achieve therapeutic efficacy because less drug is lost as a result of degradation within the stomach. Once released, and due to the proximity within the G.I. tract, the drug stabilized through the use of a vesicle or enteric coating is more readily available for absorption through the intestine.

In addition, the vesicle employed can be selected to improve the bioavailability of a drug by bypassing the liver and taking the drug directly into the lymphatic system. For example, Peyer's patches are regions lining approximately 25% of the G.I. tract and function as absorption sites to the lymphatic system. Vesicles, such as liposomes, have been shown to be preferentially taken up by Peyer's patches. By incorporating an antigen-associated liposome into the dosage forms of the present invention, controlled and continuous delivery of the antigen to the lymphoid system over a period of several hours is possible as a result of the preferential absorption of the liposome by the Peyer's patches.

Also, the liposome provides further protection of the drug from the time it leaves the dosage form until it reaches the absorption site. By delivering the antigen in this manner, there is no longer a need to ingest large amounts of the antigen to avoid degradative gastric acidity and proteolytic enzymes. Methods for preparing liposome encapsulated drug systems are known to and used by those of skill in the art. A general discussion, which includes an extensive bibliography regarding liposomes and methods for their preparation, can be found in "Liposomes, A Practical Approach, R.R.C New, ed, 1990, incorporated herein by reference.

Further examples of such vesicles include microparticulate systems which are exemplified by nanoparticles and proteinoid and amino acid microspheres and pharmacosomes. Nanoparticles include, for example, nanospheres and nanocapsules. The matrix-like structure of the nanosphere allows the drug to be contained either within the matrix or coated on the outside. Nanocapsules have a shell of polymeric material and, as with the nanospheres, the drug can be contained either within the shell or coated on the outside. Polymers which can be used to prepare the nanoparticles include, but are not limited to, polyacrylamide, poly(alkyl methacrylates), poly(alkyl cyanoacrylates), polyglutaraldehyde, poly(lactide-co-glycolide) and albumin. For details pertaining to nanoparticle preparation, see, e.g., Allemann, E., et al., Drug-Loaded Nanoparticles—Preparation Methods and Drug Targeting Issues, Eur. J. Pharm. Biopharm., 39(5):173–191, 193, incorporated herein by reference.

By incorporating drugs or drug-containing vesicles in the dosage forms of the invention, macromolecules, such as peptides, proteins, immunoglobulins and polynucleotides, that are currently administered by injection can be orally delivered to achieve therapeutic effects. In addition, bacteria or inactivated viruses for eliciting an immunological response can be carried out by the dosage forms of the present invention to achieve an effective modality for oral vaccination. Examples of drugs which can be advantageously incorporated into a protective vesicle are antigens, as exemplified by carbohydrates, lipids, proteinaceous materials and inactivated viruses. Such antigens are combined with the vesicle and orally administered via the dosage forms of the present invention to induce an immune response.

As noted above, when employing protective vesicles, the drug need not be sparingly soluble. Thus, the dosage forms of the invention are applicable to drugs of higher solubility in that the rate at which the drug solubilizes is retarded due to the vesicle as it is bound up with the dosage form. As the dosage form erodes, the vesicle containing the drug is freed to the G.I. tract and allowed to pass into the intestines. As a result, a higher amount of drug is retained in the stomach for a longer period of time when compared to the administration of either drug alone or the drug within the vesicle in the absence of the dosage form.

The solid drug(s), drug(s)/vesicle or drug(s)/enteric coating are dispersed in a polymer having the characteristics and properties described above. In a preferred embodiment, the polymer used is a poly(ethylene oxide) polymer. Other polymers having properties similar to poly(ethylene oxide) and which can be used in the present invention will be known to those of skill in the art. The hydrophilicity and water swellability of these polymers cause the drug-polymer particles to swell in size as the water of the gastric cavity is imbibed into the particle. Soon after swelling is initiated, the outer surfaces of the particle starts to erode. As soon as erosion starts and as it progresses, drug(s), drug(s)/vesicle or drug(s)/enteric coating is released into the stomach. The release rate from the particles is primarily dependent upon the rate at which the polymer erodes which, in turn, is related to the type of polymer employed, the molecular weight of the polymer, the particle size and surface area, and the ratio of drug(s), drug(s)/vesicle or drug(s)/enteric coating to polymer which can also be expressed as the drug concentration in the particle. Correlatively, because these polymers erode at a gradual rate in gastric fluid, the particles characteristically decrease in size over the entire portion of the intended dosing period, after first swelling to a maximum size.

All the different molecular weight polymers of poly (ethylene oxide) having suitable properties as noted above can be used to prepare the dosage forms of the present invention. Poly(ethylene oxide) is used herein to refer to a linear polymer of unsubstituted ethylene oxide. The molecular weight of the poly(ethylene oxide) polymers can range from about $9 \times 10^5$ to about $8 \times 10^6$. A preferred molecular weight poly(ethylene oxide) polymer is about $5 \times 10^6$ and is commercially available from Union Carbide Corporation Specialty Chemicals (Danbury, Conn.) referred to as SENTRY® POLYOX® water-soluble resins, NF (National Formulary) grade WSR Coagulant. It has a viscosity of a 1% solution at 25° C. of from 4500 to 7500 centipoise.

The drug/polymer mixture is in the form of a plurality of particles. The solid drug is preferably dispersed homogeneously in the polymer, although it need not be. The weight ratio of drug to polymer in the mixture or dispersion will normally be about 2:3 to 9:1, preferably about 3:2 to 9:1, and most preferably about 4:1 to 9:1. The particles are cylindrical or spherical in shape, preferably cylindrical, but may be in the shape of less regular granules.

The swollen particles will be of a size that promotes their retention in the stomach when the patient is in the fed mode (i.e., presence of food). This will normally be in the range of about 2 to about 22 mm, preferably about 8 to about 18 mm (measured as the diameter for spherical particles or largest dimension for irregularly shaped particles), but may be larger. Since the particles will typically swell up to twice their original diameter in from 2 to about 4 hours, the initial particle size is usually in the range of about 3 to 11 mm, preferably about 4 to 10 mm. Because the particles will gradually erode during the dosing period, their swollen volume will decrease over the dosing period.

The particles may be formed into a packed mass for ingestion by conventional techniques. For instance, the particles may be encapsulated as a "hard-filled capsule" or a "soft-elastic capsule" using known encapsulating procedures and materials. The encapsulating material should be highly soluble in gastric fluid so that the particles are rapidly dispersed in the stomach after the capsule is ingested. Each unit dose, whether capsule or tablet, will preferably contain particles of a size which when swollen enhance the potential for gastric retention. With respect to the number of particles per unit dose, a useful quantity for addition to a size O capsule is from 2 to 5 spherical or cylindrical pellets, 3 to 7 mm in diameter, and 4 to 11 mm in length. The size O capsule may contain 3 such pellets 6.5 mm long; 2 of 10 mm length; 4 of 5 mm length; or 5 or 4 mm length. Ideally, the dosage form will consist of a size O gelatin capsule containing 2 cylindrical pellets about 6.6 mm in diameter and about 10.2 mm in length.

The particulate drug/polymer mixture can be made by a number of mixing and comminution techniques with the final particle being fabricated by one of the following two methods:

(1) Direct compression, using multicavity hemispherical punches and dies, available from Elizabeth Carbide Die Company, Inc., McKeesport, Pa. The punches and dies are fitted to a suitable rotary tableting press, such as the Elizabeth-Hata single-sided Hata Auto Press machine, with either 15, 18 or 22 stations, and which is available from Elizabeth Hata International, Inc., North Huntington, Pa.

(2) Injection or compression molding using suitable molds fitted to a compression unit, such as is available from Cincinnati Milacron, Plastics Machinery Division, Batavia, Ohio.

When direct compression is used as the manufacturing process to make pellets, the addition of lubricants may be helpful and often are important for preventing "capping" of the particle when the pressure is relieved. This is increasingly important as smaller spheres or particles are made. Useful agents include, but are not limited to, magnesium stearate (in a concentration in the powder mix of from 0.25% to 5%, preferably about 0.5% by weight), and hydrogenated vegetable oil (about 1% to 5% by weight, preferably about 1% by weight). Hydrogenated vegetable oil is a National Formulary (NF) substance comprising hydrogenated and refined triglycerides of stearic and palmitic acids.

Alternatively, capping may be eliminated with lower concentrations of the lubricants or other excipients if a unit shape is chosen part way between a sphere and a right cylinder. This is the case, for instance, if the unit is a cylinder with convex, instead of flat, ends. Thus, another embodiment of the invention is a plurality of pellets, instead of spheres, which are either prolate or oblate spheroids or cylinders of approximately equant dimensions. That is, the diameter of the circular cross-section is near, but is not equal to the length of the axis normal to the section. As with the sphere dimensions described elsewhere, this dimension is from about 3 to about 11 mm, and preferably from about 4 to about 10 mm.

The dose of drugs from conventional medication forms is specified in terms of drug concentration and administration frequency. In contrast, because the dosage forms of the present invention deliver a drug by continuous, controlled release, a dose of medication used in the disclosed systems is specified by drug release rate and by duration of the release. The continuous, controlled delivery feature of the system allows for (a) a reduction in drug side effects, since only the level needed is provided to the patient, and (b) a reduction in the number of administrations per day.

Different drugs have different biological half-lives which determine their required frequency of administration (once daily, four times daily, etc.). Thus, when two or more drugs are co-administered in one conventional medication unit, an unfavorable compromise is often required, resulting in an underdose of one drug and an overdose of the other. One of the advantages of the dosage forms of the present invention is that they can be used to deliver multiple drugs without requiring such compromises. For example, in an alternative embodiment, a plurality of drug-containing, spherical, spheroidal- or cylindrical-shaped particles are provided, some of the particles containing a first drug/polymer composition designed to release the first drug at its ideal rate and duration (dose), while other particles contain a second drug/polymer composition designed to release the second drug at its ideal rate and duration. In this embodiment, the polymers or polymer molecular weight values used for each of the drugs can be the same or different. Control of the release rate of the differing drugs can also be obtained by combining different numbers of each of the drug/polymer particles in a common dosage form such as a capsule. For example, where two drugs are combined in a capsule made from five particles, three particles would contain one drug and the other two particles would contain the other drug.

Furthermore, the invention provides dosage forms of separate particles, each comprising polymers that erode at different rates. As a result, the dosage forms of the present invention achieve a plurality of drug delivery rates. For example, the dosage form may comprise three particles, the first and second containing a swellable polymer that erodes and delivers drug over a period of 4 hours, and the third containing a swellable polymer that erodes and delivers drug over a period of 8 hours. In this regard, requisite erosion rates can be achieved by combining polymers of differing erosion rates into a single particle.

Examples of drug combination products based on the invention include, but are not limited to, angiotensin converting enzyme inhibitors (ACE inhibitors) plus diuretics. Specific examples of such inhibitors are captopril or enalopril, and examples of diuretics include triampterine and hydrochlorothiazide. Alternatively, either of these diuretics can advantageously be used in combination with a beta adrenergic blocking agent such as propranolol, timolol and metaprolol.

These particular combinations are useful in cardiovascular medicine, and provide advantages of reduced cost over separate administrations of the different drugs, plus the particular advantage of reduced side effects and enhanced patient compliance. For example, it has been shown that small doses of a diuretic plus small doses of either an ACE inhibitor or a beta blocker provide the additive effects of lowering blood pressure without the additive side effects of the two together.

In addition, the invention provides dosage forms of separate particles, some comprising polymers that swell, but do not erode and some comprising polymers that swell and erode (with either the same or differing erosion rates). As a result, the dosage forms achieve a plurality of delivery rates. For example, the dosage form may comprise three particles, the first containing a swellable polymer that delivers drug over a period of 8 hours, the second containing a swellable/erodible polymer that erodes and delivers drug over a period of 4 hours, and the third containing a swellable/erodible polymer that erodes and delivers drug over a period of 6 hours. In this example, the dosage form may contain one, two or three different drugs.

Furthermore, drugs that are otherwise chemically incompatible when formulated together can be delivered simultaneously via separate swellable particles contained in a single dosage form. For example, the incompatibility of aspirin and prednisolone can be overcome with a dosage form comprising a first swellable particle with one drug and a second swellable particle with the other. In this manner, the gastric retention and simultaneous delivery of a great number of different drugs is now possible.

The invention will be described in greater detail by way of specific examples. The following examples are offered for illustrative purposes, and are intended neither to limit nor define the invention in any manner.

EXAMPLES

A. Example 1

Four 4-mm pellets, each weighing approximately 90 mg, are made from barium sulfate, an insoluble agent, and one of the polymers listed in Table 1, using a 4-mm punch and die and a manual pellet press.

Each pellet is weighed immediately before placement into stirred gastric fluid, which is modified to exclude pepsin, at 37° C. At specific time points, the pellets are removed from the gastric fluid and placed in a petri dish to dry. Once dried, the remaining polymer-drug mixture is carefully scraped off the petri dish and weighed. The difference between the final and initial weight is taken to represent the amount of barium sulfate/polymer lost through erosion.

TABLE 1

Polymers Tested for Erosion Characteristics

| Polymer | Chemical Name | Barium Sulfate Loading |
|---|---|---|
| Benecel MP843 | Hydroxypropyl methylcellulose | 80% |
| Metolose 4000 | Hydroxypropyl methylcellulose | 70% |
| Polyox Coagulant | Poly(ethylene oxide) | 80% |
| Polyox N-80 | Poly(ethylene oxide) | 60% |

Figure 2:
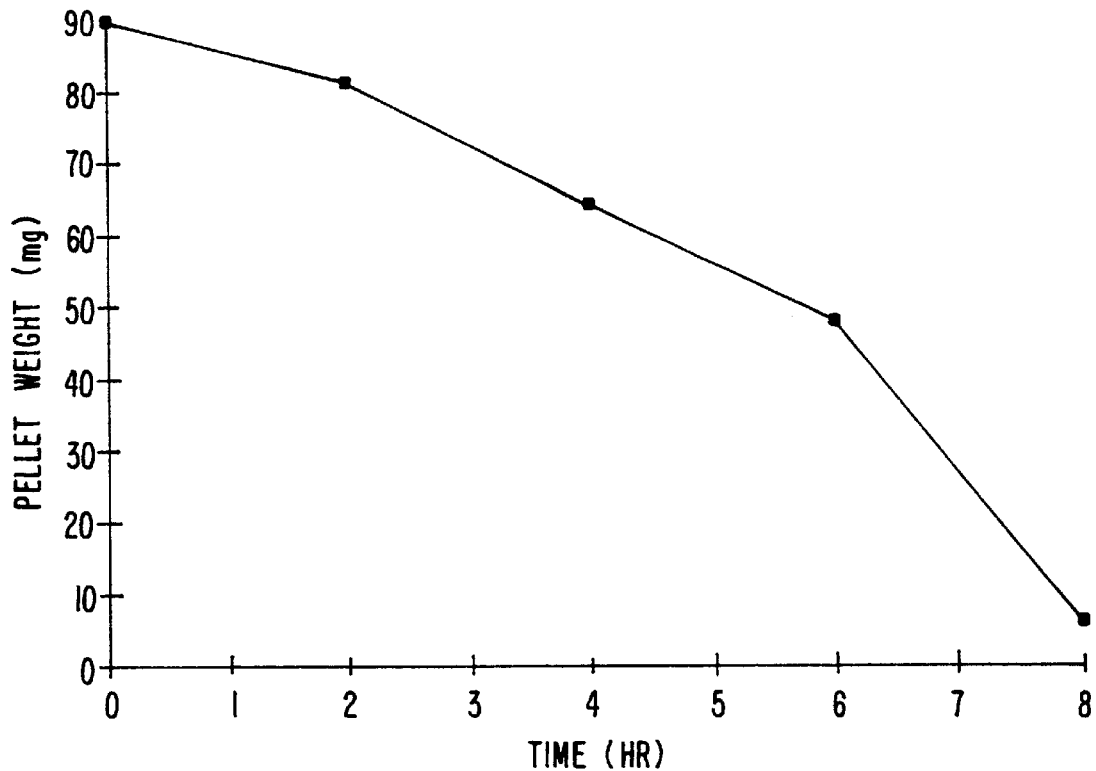
FIG. 2 illustrates the erosion of a 4-mm pellet containing 70% barium sulfate in Polyox® Coagulant (poly(ethylene oxide)), M.W. $5 \times 10^6$].

The erosion rates for the barium sulfate/Benecel® (hydroxypropyl methylcellulose) pellets and the barium sulfate/Polyox® (polyethylene oxide) pellets are shown graphically in FIGS. 1 and 2, respectively. Both polymers gradually eroded over the 8 hour time period the analysis was carried out.

B. Example 2

Three 4-mm pellets, each weighing approximately 122 mg, are made with barium sulfate (to exemplify an insoluble drug) and one of the polymers listed in Table 2, using a 4-mm punch and die in a manual pellet press.

TABLE 2

Polymers Tested for Swelling and Erosion Characteristics

| Polymer | Chemical Name | Barium Sulfate Loading | Other |
|---|---|---|---|
| Benecel MP843 | Hydroxypropyl methylcellulose | 80% | medium viscosity |
| Benecel MP824 | Hydroxypropyl methylcellulose | 85% | high viscosity |
| Metolose 4000 | Hydroxypropyl methylcellulose | 70% | medium viscosity |
| Polyox N-750 | Poly(ethylene oxide) | 15% | 300,000 MW |
| Polyox Coagulant | Poly(ethylene oxide) | 80% | 5,000,000 MW |
| Polyox 303 | Poly(ethylene oxide) | 80% | 7,000,000 MW |

Figure 3:
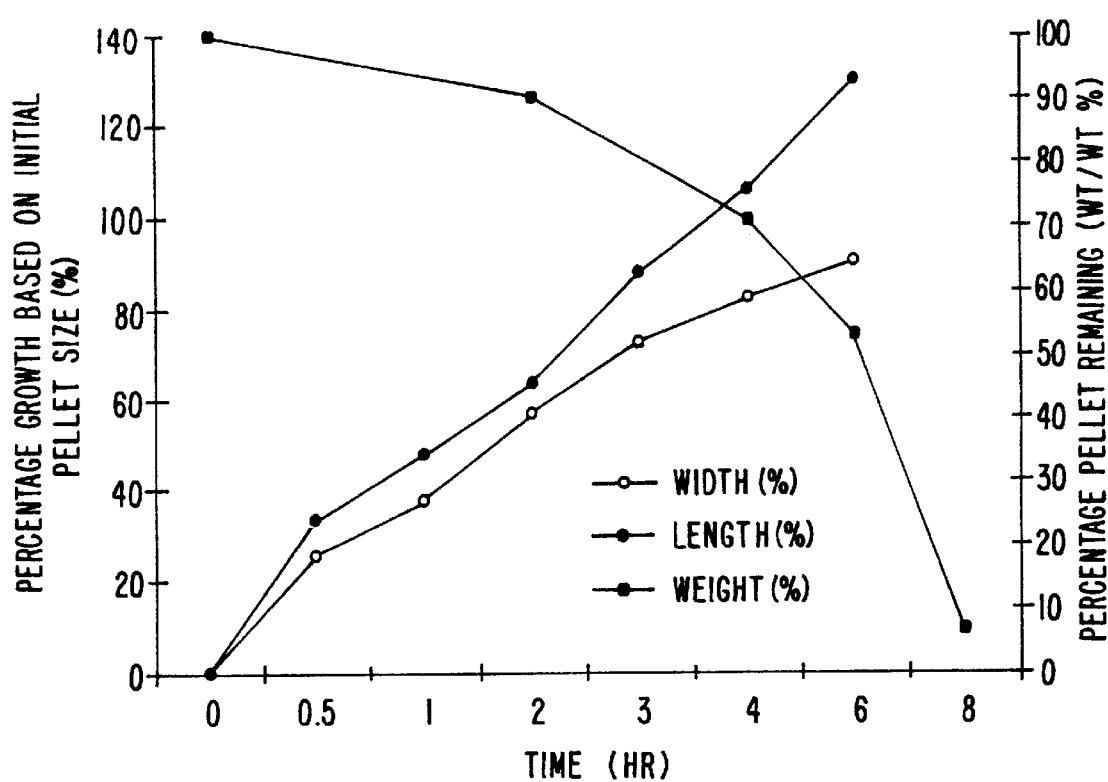
FIG. 3 illustrates the swelling and erosion of a 4-mm pellet containing 70% barium sulfate in Polyox® Coagulant (poly(ethylene oxide)) in stimulated gastric fluid at 37° C.

Each pellet is measured (both length and width) immediately prior to placement into gastric fluid (which is modified to exclude pepsin) at 37° C. Immediately after exposure to the modified gastric fluid, the pellets are measured for the zero hour time point. The pellets are again measured at 0.5, 1, 2, 3, 4 and 6 hours. Each dimension is averaged for each time point and the swelling rate is determined by calculating the percent growth in each dimension compared to the time zero dimensions. All pellets are found to swell during the time period observed. As an example, the swelling and erosion rate for barium sulfate in Polyox® Coagulant is shown graphically in FIG. 3.

C. Example 3

This example illustrates the steps involved in manufacturing the dosage forms of the present invention.

A two kilogram batch is prepared by first combining 1592 grams of acyclovir with 398 grams of polyethylene oxide, and 5 grams of magnesium stearate. This mixture is placed into an eight quart, twin-shell blender (Patterson-Kelly Company, East Stroudsburg, Pa.) and dry-mixed for five minutes.

The dry blended mixture is then subjected to a precompression step using a roller compactor, model TF-Mini (Vector Corporation, Marion, Iowa). The resultant compacts are dry-milled using a CoMil, model 197-S grinder (Quadro Engineering, Waterloo, ON, Canada). An additional 5 grams of magnesium stearate is combined with the milled granulation, and then dry-mixed for three minutes in a twin-shell blender.

The dry granulation, prepared as described above, is directly compressed into cylindrical tablets (6 mm diameter×6 mm height) utilizing a single-station tablet press, model F 4 (F.J. Stokes Corporation, Philadelphia, Pa.), fitted with six millimeter, standard cup tooling (Natoli Engineering, Chesterfield, Mo.).

Tablets are then filled into size 0, hard-shell, gelatin capsules, three tablets per capsule, utilizing an automatic capsule filling machine fitted with standard tablet feeder(s), model GKF 400 (Robert Bosch, Minneapolis Minn.).

The release rate of acyclovir from the tablet-containing capsules, as determined over a period of 8 hours in simulated gastric fluid at 37° C., is found to be relatively constant up to the time of delivery of 90% of the total content, which occurs at approximately 6 hours.

D. Example 4

Materials for clinical trials are prepared as described in Example 3, except that the pellets have the following composition: 40% barium sulfate; 59.75% polyethylene oxide; and 0.25% magnesium stearate. The barium sulfate allows for visualization of the position of the pellets in the gastrointestinal tract of the human subjects over the time course of the study using X-radiology.

Ten normal human subjects who fit the selection criteria are administered one size 0 gelatin capsule containing three 6 mm (diameter) by 6 mm (length) cylindrical pellets of the above composition, immediately following a standard meal consisting of 30% fat. Thus, subjects enter the fed mode while the ingested capsule dissolves, allowing the pellets to rapidly swell to approximately twice their initial size.

Progress of the pellets through the gastrointestinal tract is monitored in each subject by X-radiology at 2, 4, 6, 8 and 10 hours post instillation. The results obtained support the conclusion that the oral delivery system is retained in the stomachs of human subjects for a period averaging from six to eight hours.

E. Example 5

This example describes vesicles containing the anti-AIDS drug zidovudine (AZT) which, in clinical use, are continuously delivered by the dosage form of the invention. The continuous, controlled delivery of the dosage forms of the present invention allows for a reduction of very formidable side effects of the drug. Moreover, by largely overcoming problems resulting from the short half-life of the drug, the dosage forms of the present invention allow for a less frequent administration regimen. Incorporation of this drug in vesicles, such as liposomes, promotes the targeting of organs where macrophages are heavily concentrated, i.e., areas of high levels of HIV infection, but not areas that are reached by the drug when administered by conventional dosage forms.

200 mg of a mixture of egg lecithin, cholesterol, and phosphatidyl glycerol in the molar ratio of 0.9:1.0:0.1 are added to 100 ml of an organic solvent consisting of 2:1 chloroform:methanol. This lipid solution is evaporated to dryness in a rotary evaporator with a vacuum for a period of time sufficient to assure loss of all chloroform. The residue is then dissolved in 100 ml of ether. 200 mg of zidovudine is dissolved in 50 ml of distilled water, and the solution heated to 55° C. The ether solution is injected below the surface of the warm aqueous solution at an approximate rate of 0.1 ml per minute using a 22 g. hypodermic needle. The liposomes formed are collected by centrifugation, washed with distilled water and dried under vacuum. The concentration of zidovudine in the liposomes is determined by assay following destruction of a weighed sample by action of an organic solvent.

A sufficient weight of liposomes thus prepared and assayed are added to a polyethylene oxide polymer (Polyox 301) so that the ratio of zidovudine to polymer is 4:1. Following mixing in a twin-shell blender, the mixture is compressed into 6 mm (diameter)×6 mm (height) cylindrical pellets, for fabrication into the dosage form of the invention as described in Example 3.

F. Example 6

This example illustrates the use of a dosage form containing an enteric-coated drug.

The dosage form is prepared as described in Example 3, except the drug is calcitonin, and the drug is pre-treated prior to the initial blending with the polymer and lubricant. In the pre-treatment process, the drug crystals are enteric-film coated with a methacrylic acid copolymer utilizing a bottom spray fluid bed, model GPCG-1, with a Wurster HS processing insert (Glatt Air Techniques, Ramsey, N.J.). The enteric-film coated drug crystals are further processed as described in Example 3.

The enteric coating protects the calcitonin from degradation resulting from the effects of low pH and stomach enzyme. Thus, the dosage forms of the present invention provide continuous, controlled delivery of undegraded calcitonin over a period of several hours to the upper part of the small intestine, the site where the enteric coating dissolves and, thus, where the calcitonin dissolves, and the site of most efficient absorption of this macromolecule. This protection and enhanced absorption allows for the effective oral administration of a drug that otherwise requires administration by injection.

G. Example 7

This example illustrates the use of a gastric-retentive dosage form that provides for the controlled delivery of two drugs, each at its proper rate for therapeutic effectiveness, from once-daily administration.

The effective management of a number of disease conditions often requires the concomitant use of two drugs. For instance, the successful treatment of arterial hypertension often requires the administration of both a calcium channel blocker and a diuretic. To date, a combination product, i.e., a single product with more than one principal drug, has not been possible with these drugs as a result of their widely different biological half-lives which, in turn, results in different requirements regarding the frequency of their administration. Thus, a proper regimen for one drug would result in either an over- or an under-dose for the other.

The multi-particulate dosage forms of the present invention provide a solution to this problem. More particularly, the multi-particulate dosage forms of the present invention allow for the use of pellets of different polymers for each drug to be delivered, thereby allowing release rates and release durations that are different, but optimal for each drug to be delivered. Alternatively, this objective can be accomplished by employing different polymer molecular weight values or different drug loading factors, or combinations thereof.

In this example, two very sparingly soluble drugs, nifedipine (a calcium channel blocker) and triamterine (a diuretic) are combined in the dosage form, with one polymeric pellet for each drug, with both pellets contained in a single size 0 gelatin capsule. One pellet contains 90 mg of nifedipine and 210 mg of polyethylene oxide having a molecular weight of 2,000,000; whereas, the other pellet contains 150 mg of triamterine and 150 mg of polyethylene oxide having a molecular weight of 5,000,000. When placed in artificial gastric fluid at 37° C., this dosage form releases both drugs in a controlled manner so that 90% of each drug is delivered within eight hours.

It is to be understood that the above descriptions are intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purposes.

What is claimed is:

1. A controlled release oral drug dosage form for releasing a sparingly soluble drug into the stomach, duodenum and upper small intestine of a patient, said drug dosage form comprising: a plurality of solid particles consisting of said drug dispersed within a polymer that (i) swells unrestrained dimensionally via imbibition of water from gastric fluid to increase the size of the particles to promote gastric retention in the stomach of said patient in which the fed mode has been induced, (ii) gradually erodes over a time period of hours, said erosion commencing upon contact with said gastric fluid, and (iii) releases said drug to the stomach duodenum and upper small intestine of said patient, as a result of said erosion at a rate corresponding to said time period; wherein said polymer is poly(ethylene oxide).

2. The dosage form in accordance with claim 1 wherein the dosage form is in the form of a tablet or capsule that packages said solid particles prior to their ingestion and then dissolves upon contact with the gastric fluid to permit said solid particles to disperse in the stomach.

3. The dosage form in accordance with claim 1 wherein said poly(ethylene oxide) has a molecular weight of between about $9 \times 10^5$ kD and $8 \times 10^6$ kD.

4. The dosage form in accordance with claim 3 wherein said poly(ethylene oxide) has a molecular weight of between about $1 \times 10^6$ kD and $7 \times 10^6$ kD.

5. The dosage form in accordance with claim 1 wherein said drug is a member selected from the group consisting of nifedipine, acyclovir, alprazolam, phenytoin, carbamazepine, ranitidine, cimetidine, famotidine, clozapine, nizatidine, omeprazole, gemfibrozil, lovastatin and nitrofurantoin.

6. The dosage form in accordance with claim 1 wherein said drug is a *Helicobacter pylori* eradicant.

7. The dosage form in accordance with claim 6 wherein said eradicant is a member selected from the group consisting of bismuth subsalicylate, bismuth citrate, amoxicillin, tetracycline, chlarithromycin, thiamphenicol, metronidazole, omeprazole, ranitidine, cimetidine, famotidine and combinations thereof.

8. The dosage form in accordance with claim 7 wherein said eradicant is bismuth subsalicylate.

9. The dosage form in accordance with claim 8 wherein the controlled time period is about 6 to 8 hours, and the dose of said bismuth subsalicylate is 200–800 mg.

10. The dosage form in accordance with claim 1 wherein said solid particles are about 6–13 mm in length in maximum dimension prior to swelling.

11. The dosage form in accordance with claim 1 wherein said solid particles are about 7–11 mm in length in maximum dimension prior to swelling.

12. The dosage form in accordance with claim 1 wherein said solid particles are about 3–10 mm in diameter prior to swelling.

13. The dosage form in accordance with claim 1 wherein said solid particles are about 5–7 mm in diameter prior to swelling.

14. The dosage form in accordance with claim 2 wherein said dosage form is a size 0 capsule, the particles are about 5–7 mm in diameter and number about 2–3 in one capsule.

15. The dosage form in accordance with claim 9 wherein said drug is in a vesicle.

16. The dosage form in accordance with claim 15 wherein said vesicle is a member selected from the group consisting of liposomes, nanoparticles, pharmacosomes and proteinoid or amino acid microspheres.

17. The dosage form in accordance with claim 1 wherein said solid particles consist of a first drug dispersed within a first swellable/erodible polymer and a second drug dispersed within a second swellable/erodible polymer, said first and second swellable/erodible polymers exhibiting different erosion rates.

18. The dosage form in accordance with claim 17 wherein said first drug is chemically incompatible with said second drug.

19. The dosage form in accordance with claim 1 wherein said solid particles consist of particles comprising a first drug and particles comprising a second drug.

20. The dosage form in accordance with claim 1 wherein said drug is calcium carbonate, and wherein the gastric retention in the stomach and the erosion time of said solid particles assure a substantially complete dissolution of said drug in the acid environment of the stomach.

21. A controlled release oral drug dosage form for releasing a vesicle-containing drug into the stomach, duodenum, and intestinal areas which contain Peyer's patches of a patient, said dosage form comprising a plurality of solid particles consisting of said vesicle-containing drug dispersed within a polymer that (i) swells unrestrained dimensionally via imbibition of water from gastric fluid to increase the size of the particles to promote gastric retention in the stomach of said patient in which the fed mode has been induced, (ii) gradually erodes over a time period of hours, said erosion commencing upon contact with said gastric fluid, and (iii) releases said vesicle-containing drug to the stomach, duodenum, and intestinal areas which contain Peyer's patches of said patient, as a result of said erosion at a rate corresponding to said time period; wherein said polymer is poly(ethylene oxide).

22. The dosage form of claim 21 wherein said drug is soluble, but is rendered sparingly soluble when contained in said vesicle.

23. The dosage form in accordance with claim 21 wherein said vesicle is a member selected from the group consisting of a liposome, nanoparticle, nanosphere and nanocapsule.

24. The dosage form in accordance with claim 21 wherein said solid particles consist of a first drug dispersed within a first swellable/erodible polymer and a second drug dispersed within a second swellable/erodible polymer, said first and second swellable polymers exhibiting different erosion rates.

25. The dosage form in accordance with claim 24 wherein said first drug is chemically incompatible with said second drug.

26. A controlled release oral drug dosage form for releasing an enteric-coated drug into the stomach, duodenum and upper small intestine of a patient, said dosage form comprising a plurality of solid particles consisting of said enteric-coated drug dispersed within a polymer that (i) swells unrestrained dimensionally via imbibition of water from gastric fluid to increase the size of the particles to promote gastric retention in the stomach of said patient in which the fed mode has been induced, (ii) gradually erodes over a time period of hours, said erosion commencing upon contact with said gastric fluid, and (iii) releases said enteric-coated drug to the stomach, duodenum and upper small intestine of said patient, as a result of said erosion at a rate corresponding to said time period; wherein said polymer is poly(ethylene oxide).

27. The dosage form of claim 26 wherein said drug is soluble, but is rendered sparingly soluble when enteric-coated.

28. The dosage form in accordance with claim 26 wherein the enteric-coating is a member selected from the group consisting of methacrylic acid copolymer and water-based dispersions of cellulose acetate phthalate latex.

29. The dosage form in accordance with claim 26 wherein said solid particles consist of a first drug dispersed within a first swellable/erodible polymer and a second drug dispersed within a second swellable/erodible polymer, said first and second swellable polymers exhibiting different erosion rates.

30. The dosage form in accordance with claim 29 wherein said first drug is chemically incompatible with said second drug.

31. A method for delaying the passage of a sparingly soluble drug through the gastrointestinal tract of a patient, said method comprising: providing a dosage form consisting of a plurality of solid particles consisting of a solid-state drug dispersed within a polymer that (i) swells unrestrained dimensionally via imbibition of water from gastric fluid to increase the size of the particles to promote gastric retention in the stomach of said patient in which the fed mode has bean induced, (ii) gradually erodes over a time period of hours, said erosion commencing upon contact with said gastric fluid, and (iii) releases said drug to the stomach, duodenum and upper small intestine, as a result of said erosion at a rate dependent on said time period; and introducing said dosage form to said patient orally; wherein said polymer is poly(ethylene oxide).

32. The drug dosage form in accordance with claim 1 wherein the dosage form is in the form of a tablet.

33. The drug dosage form in accordance with claim 1 wherein the dosage form is in the form of a capsule.

* * * * *